United States Patent [19]
Itoh et al.

[11] Patent Number: 5,508,363
[45] Date of Patent: Apr. 16, 1996

[54] PREPARATION PROCESS OF ORGANOSILICON COMPOUNDS AND PRODUCTION OF SILICON CARBIDE

[75] Inventors: Masayoshi Itoh, Yokohama; Ryo Takeuchi, Kamakura; Kenji Iwata, Yokohama, all of Japan

[73] Assignee: Mitsui Toatsu Chemicals, Incorporated, Tokyo, Japan

[21] Appl. No.: 413,115

[22] Filed: Mar. 29, 1995

Related U.S. Application Data

[62] Division of Ser. No. 383,712, Feb. 3, 1995, which is a division of Ser. No. 147,425, Nov. 5, 1993, abandoned, which is a continuation of Ser. No. 585,275, Sep. 17, 1990, abandoned, which is a continuation of Ser. No. 254,940, Aug. 22, 1988, abandoned.

[30] Foreign Application Priority Data

| Jan. 28, 1987 | [JP] | Japan | 62-015929 |
| Feb. 16, 1987 | [JP] | Japan | 62-031514 |
| Feb. 20, 1987 | [JP] | Japan | 035696 |
| Apr. 13, 1987 | [JP] | Japan | 62-088871 |
| Apr. 14, 1987 | [JP] | Japan | 089888 |
| Apr. 22, 1987 | [JP] | Japan | 62-097417 |
| Apr. 23, 1987 | [JP] | Japan | 62-098698 |
| Jul. 12, 1987 | [JP] | Japan | 62-307491 |
| Jul. 12, 1987 | [JP] | Japan | 62-307492 |
| Jul. 12, 1987 | [JP] | Japan | 62-307493 |

[51] Int. Cl.$^6$ ................................. C08F 4/24
[52] U.S. Cl. .......... 526/106; 526/137; 526/156; 526/176; 526/177; 526/190; 526/227; 526/237; 526/279; 526/169.2
[58] Field of Search .............. 526/279, 106, 526/156, 137, 176, 177, 190, 227, 237, 169.2

[56] References Cited

U.S. PATENT DOCUMENTS

| 2,537,763 | 9/1951 | Hurd | 260/448.2 |
| 2,786,862 | 3/1967 | Wolfe et al. | 260/448.2 |
| 3,026,213 | 3/1962 | Oppegard et al. | 106/285 |
| 3,223,686 | 12/1965 | Natta et al. | 526/279 |
| 3,385,876 | 5/1968 | Nielsen | 260/448.2 |
| 3,410,886 | 11/1968 | Joy | 260/448.2 |
| 3,644,306 | 2/1972 | Longi et al. | 526/279 |

FOREIGN PATENT DOCUMENTS

| 0052694 | 6/1982 | European Pat. Off. . |
| 1390999 | 10/1965 | France . |
| 606018 | 4/1958 | Italy . |
| 33-9969 | 11/1958 | Japan . |
| 44-25768 | 10/1969 | Japan . |
| 52-42873 | 4/1977 | Japan . |
| 57-26527 | 6/1982 | Japan . |
| 57-96020 | 6/1982 | Japan . |
| 57-38548 | 8/1982 | Japan . |
| 57-53892 | 11/1982 | Japan . |

OTHER PUBLICATIONS

Naturforsh., 56, (1950), 444.
Naturforsh., 76, (1952), 207–210 and 213–216.
Z. Anorg. Allgem. Chem., 273, (1953), 275–285.
J. Am. Chem. Soc., 76, (1954), 3897–3902.
Journal of Polymer Science, 31, No. 122, (1958), 181, 183.
Chemistry Letters, (1976), 551–554.
Chemical Abstracts, vol. 93, No. 1, (Jul. 7, 1980), 8286p.
Journal of Organometallic Chemistry, vol. 9, No. 3, (1967) 421–426.
Moriya, Uchida, "Sentan Fukugo Sairyo", (Sep. 1, 1986), Tokyo, Kogyo Chosakai, 84–86.
Tannenbaum et al., J. Am. Chem. Soc., vol. 75, (Aug. 5, 1953), pp. 3753 to 3757.
Mellor, J. W., "A Comprehensive Treatise On Inorganic And Theoretical Chemistry", vol. IX, pp. ix, x and 855.
Encyclopaedia Chimica, vol. 5, p. 58.
Encyclopaedia Chimica, vol. 1, p. 103.
Encyclopaedic Dictionary Of Chemistry, p. 30.

*Primary Examiner*—Mark D. Sweet
*Attorney, Agent, or Firm*—Fisher, Christen & Sabol

[57] ABSTRACT

Disclosed herein are a novel process for the preparation of alkylsilanes and alkenyl silanes by hydrosilylation of their corresponding silanes and unsaturated hydrocarbons in the presence or absence of a catalyst, a process for the preparation of polyalkenylsilanes (some of which are novel high molecular compounds) by the anionic coordination polymerization, radical polymerization or ionic polymerization of the alkenylsilanes, and a process for the production of silicon carbide by using these polyalkenylsilanes as prepolymers.

3 Claims, 1 Drawing Sheet

PREPARATION PROCESS OF ORGANOSILICON COMPOUNDS AND PRODUCTION OF SILICON CARBIDE

This is a divisional application of Ser. No. 08/383,712, filed on Feb. 3, 1995, which is a divisional application of Ser. No. 08/147,425, filed on Nov. 5, 1993, now abandoned, which is a continuation application of Ser. No. 07/585,274, filed on Sep. 17, 1990, now abandoned, which is a continuation application of Ser. No. 07/254,940, filed on Aug. 22, 1988, now abandoned.

TECHNICAL FIELD

This invention relates to a novel process for the preparation of alkylsilanes and alkenylsilanes, a process for the preparation of silicon-containing polymers by subjecting certain specific alkenylsilanes to anionic coordination, radical or ionic polymerization, and a process for the production of silicon carbide by firing some specific polyolefins which contains silyl groups in side chains.

BACKGROUND ART

"Organosilicon compound" is a generic term for compounds which generally contain one or more Si—C bonds. The organosilicon-related chemical industry is now growing rapidly, as typified by silicones (polyorganosiloxanes). Several processes have been known for the preparation of organosilicon compounds. The following processes may be mentioned as representative ones.

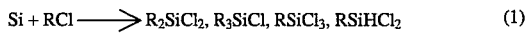  (1)

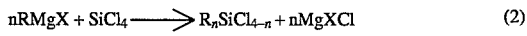  (2)

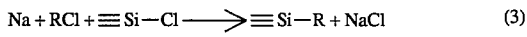  (3)

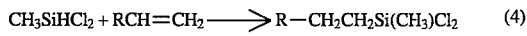  (4)

  (5)

  (6)

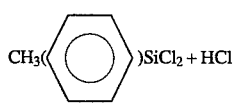

The process (1) is the Rochow's direct process, in which an organosilicon compound is prepared directly from metallic silicon and a halogenated hydrocarbon. It is a process useful for the preparation of alkylchlorosilanes, which are the most important basic starting materials in the present organosilicon industry. As halogenated hydrocarbons RCl, methyl chloride and chlorobenzene are used industrially. Other halogenated hydrocarbons give unduly low yields and are hence not suitable for industrial application.

On the other hand, the process (2) is a Grignard process while the process (3) is a dechlorination process making use of metallic sodium. These processes permit introduction of a desired alkyl group but Grignard reagents and metallic sodium are expensive and uneconomical.

The process (4) is a process similar to the present invention, but is accompanied by a serious problem that its raw material is limited to $HSiCl_3$, $CH_3SiHCl_2$ byproduced in the direct process, or the like.

Further, the processes (5) and (6) both involve high-temperature reactions and their raw materials are limited extremely, for example, to

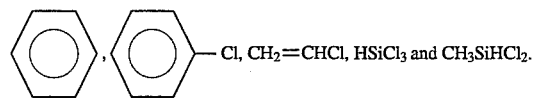

As has been mentioned above, basic raw materials of the present organosilicon industry are mostly methyl- or phenylchlorosilanes. Using these silicon compounds as starting raw materials, various functional materials such as silicones, silane coupling agents and silylating agents have been developed.

However, the conventional processes of the organosilicon industry, which employ chlorosilanes as basic raw materials, are generally accompanied by the following problems. Firstly, process equipment is subjected to considerable corrosion since the raw materials contain chlorine and hydrogen chloride is hence given off. Secondly, the processes involve many reaction steps and are hence complex. Thirdly, methylchlorosilanes are used principally due to a raw-material-related limitation and at least one of alkyl groups is a methyl group.

Regarding the synthesis of an alkylsilane or alkenylsilane by hydrosilylation (addition reaction) of $SiH_4$ and an alkene or alkyne, there have been reported only a few research results because of difficulties in obtaining $SiH_4$ and its high price. Included in such reports are Naturforsch. 56, 444 (1950); ibid 76, 207 (1952); Z. Anorg. Allgem. Chem. 273, 275 (1953); J. Am. Chem. Soc. 76, 3897 (1954); and U.S. Pat. No. 2,786,862 (1957). According to these reports, the reaction temperatures were as high as 400°–500° C. and the reactions were non-catalytic pyrolytic reactions. Furthermore, the yields were low and the selectivity to the resulting silane compounds was not controlled sufficiently. Absolutely no report has been made to date regarding hydrosilylation of $Si_2H_6$ or $Si_3H_8$.

The current principal application of silicon-containing polymers in the industry is as silicones (organopolysiloxanes). Their raw materials are alkyl-chlorosilanes produced by the reaction of metallic silicon and their corresponding halogenated hydrocarbons, namely, by the so-called direct process, in particular, dimethyldichlorosilane. Besides silicones, there are only a few practical application examples of silicon-containing polymers. The following silicon-containing polymers have been known by way of example:

(a) Permethylpolysilanes:

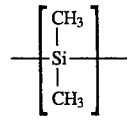

(b) Polysilastyrenes:

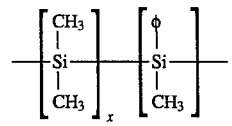

wherein X is 0.8–1.3 and φ indicates a phenyl group. This same definition will hereinafter be applied.

(c) Polycarbosilanes:

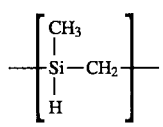

(d) Polyvinylalkoxysilanes:

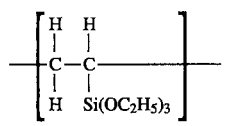

The polymers (a) are prepared in a solvent such as xylene as shown by the following equation:

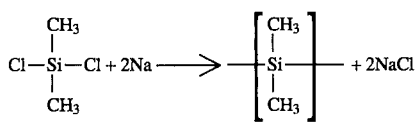

This is also applied to the polymers (b). Although the polymers (a) are insoluble and infusible, the polymers (b) are soluble in solvents and thermoplastic. The polymers (c) are obtained by subjecting the polymers (a) to pyrolysis at high temperature and pressure, and are soluble in solvents and thermoplastic. The polymers (a), (b) and (c) are employed as ceramics binders, and the polymers (b) and (c) are employed as precursors for ceramics (SIC), especially, for ceramics (SIC) fibers ("NICARON", trade mark; product of Nippon Carbon Co., Ltd.).

The preparation of silicon-containing polymers, for example, the above-mentioned polymers (a), (b) and (c) from conventional alkylchlorosilanes as raw materials is however practiced in chlorine-containing systems, so that the potential danger of corrosion of apparatus is involved. Moreover, their preparation processes are extremely complex. The polymers (d) are polymers of vinylsilane. The copolymers of vinylsilane with ethylene are used in a large volume for coating electrical wires and cables in the form of polyethylenes cross-linkable with water.

Polymers of alkenylsilanes have not been reported except for only one case in which allylsilane ($CH_2=CH=CH_2—SiH_3$) was subjected to polymerization (anionic coordination polymerization) in the presence of a Ziegler catalyst [Journal of Polymer Science, 31, No. 122, 181(1958); Italian Patent 606,018].

Considerable technological development has been made with respect to silicon-containing ceramics in recent years. For example, silicon carbide (SiC), silicon nitride ($Si_3N_4$), Cyalon, Si—Ti—C—O ceramics ("Tylano Fibers", product of Ube Industries, Ltd.), SiC-$B_4C$ ceramics, $Si_3N_4$—SiC composite ceramics and the like have attracted attention as so-called fine ceramics.

Among these, silicon carbide is available in various forms such as powder, whiskers and fibers. It has been produced by various processes. For example, there are direct carbonization, reduction carbonization, vapor-phase synthesis, pyrolysis of silicon compounds, etc.

Direct carbonization comprises reduction of metallic silicon with coke at an elevated temperature (1400°–2600° C.) and is hence economical. Fine silica $SiO_2$ powder is however indispensable for obtaining fine SiC crystals excellent in sinterability. The reaction is exothermic and its control is hence difficult.

Reduction carbonization features reduction of $SiO_2$ with coke. By reacting them at 1,500°–2,000° C. in argon, β-SiC is obtained. On the other hand, α-SiC is obtained by the Attison process which is similar to reduction carbonization. Reduction carbonization is employed principally these days in the industry.

In vapor-phase synthesis, a hydrocarbon is reacted with $SiCl_4$, $SiH_4$ or the like at 1,200° C. or higher so that silicon carbide is obtained with high purity and in the form of ultrafine powder. However, the raw material is costly and the productivity is low.

Ceramics obtained by the above-described processes are all powdery. In order to obtain shaped products from them, it is hence necessary to press and process them in the presence of a sintering agent at elevated temperature and pressure. Their processing requires an extremely large press. In addition, limitations are imposed on their shaping and processing so that products of complex configurations can hardly be fabricated.

Pyrolysis of silicon compounds features easy processing, and also features pyrolyzing, as ceramics prepolymers, linear or cyclic silicon-containing high-molecular compounds having such recurring structural units as exemplified below.

(a) Permethylpolysilanes:

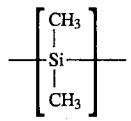

(b) Polysilastyrenes:

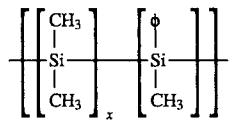

(c) Polycarbosilanes:

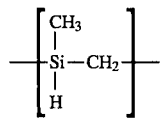

The polycarbosilanes are obtained by the pyrolysis of permethylpolysilanes or various organo-silicon compounds, for example, tetramethylsilane, dimethyldichlorosilane and dodecamethylcyclohexasilane. They are fusible and also soluble in organic solvents such as benzene. As a polycarbosilane produced presently and industrially by pyrolysis, there are SiC fibers ("NICARON", trade mark; product of Nippon Carbon Co., Ltd.). The above fibers are produced in accordance with equations (A), (B) and (C) to be described below, by using as a starting material dimethyldichlorosilane obtained by the direct process. As high-strength fibers excellent in heat resistance, their future demand as a reinforcing material for resins, metals and ceramics is expected to increase [Chemistry Letters, 551(1976); Japanese Patent Publication No. 26527/1982; Japanese Patent Publication No. 53892/1982; Japanese Patent Publication No. 38548/1982].

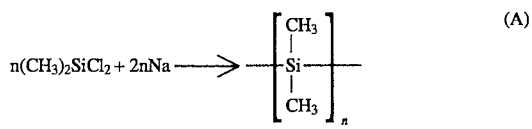

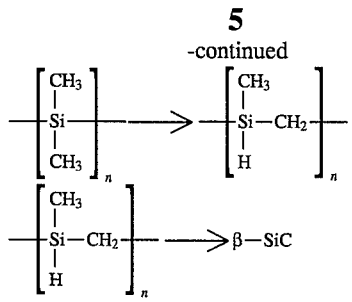

$$\left[\begin{array}{c} CH_3 \\ | \\ -Si- \\ | \\ CH_3 \end{array}\right]_n \longrightarrow \left[\begin{array}{c} CH_3 \\ | \\ -Si-CH_2- \\ | \\ H \end{array}\right]_n \quad (B)$$

$$\left[\begin{array}{c} CH_3 \\ | \\ -Si-CH_2- \\ | \\ H \end{array}\right]_n \longrightarrow \beta-SiC \quad (C)$$

It is the problem of the above process that the production steps are complex. Especially, in the step (A), the removal of unreacted sodium is cumbersome because metallic sodium is used in a solvent, and fractionation of polymers (separation and-removal of low molecular-weight polycarbosilanes) is required. In the reaction of the step (B), the reaction has to be carried out at high temperature and pressure (400° C., 100 atm). In addition, the overall yield is low [especially, in the steps (B) and (C)], and free carbon and silica which are contained in at substantial levels in final products give deleterious effects to the physical properties of the final products.

DISCLOSURE OF THE INVENTION

An object of this invention is to provide a process for economically preparing an alkyl silane or alkenylsilane by using as a starting material $SiH_4$, $Si_2H_6$ or $Si_3H_8$ whose economical industrial production has been rendered feasible.

Another object of this invention is to provide a novel polymerization process of a polymer containing silyl groups and the polymer containing silyl groups.

A further object of this invention is to provide a process for producing silicon carbide of good physical properties in a high yield and economically.

A process of this invention for the preparation of an alkylsilane or alkenylsilane comprises reacting $SiH_4$, $Si_2H_6$ or $Si_3H_8$ and an unsaturated hydrocarbon, which contains at least one carbon-carbon double bond and/or at least one carbon-carbon triple bond, in the presence of or in the absence of a specific catalyst.

A novel silicon-containing high molecular compound of this invention has recurring structural units represented by the following general formula:

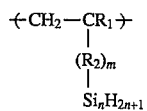

$$-(CH_2-CR_1)-$$
$$\quad\quad\quad |$$
$$\quad\quad(R_2)_m$$
$$\quad\quad\quad |$$
$$\quad\quad Si_nH_{2n+1}$$

wherein n is 1 and m is a positive integer of 5–20, or n is 2 or 3 and m is 0 or a positive integer of 1–20, $R_1$ means hydrogen, an alkyl group, an aryl group or a halogen, $R_2$ denotes an alkylene or phenylene group, and $R_1$ and $R_2$ may optionally contain one or more functional groups such as COOH, $NH_2$, Cl and OH.

By anionic coordination polymerization (where n is 1 and m is a positive integer of 5–20, or where n is 2 or 3 and m is 0 or a positive integer of 1–20) or radical polymerization or ionic polymerization (where n stands for 1, 2 or 3) of an organosilicon compound represented by the following general formula:

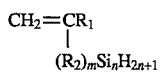

$$CH_2=CR_1$$
$$\quad\quad |$$
$$(R_2)_m Si_n H_{2n+1}$$

wherein n is 1, 2 or 3, m is 0 or a positive integer of 1–20, $R_1$ means hydrogen, an alkyl group, an aryl group or a halogen, $R_2$ denotes an alkylene or phenylene group, and $R_1$ and $R_2$ may optionally contain one or more functional groups such as COOH, $NH_2$, Cl and OH, a polymer having the corresponding recurring structural units is obtained.

Further, silicon carbide is produced by firing at a temperature in a range of 500°–2,500° C. a silicon-containing high-molecular compound having recurring structural units represented by the following general formula:

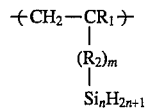

$$-(CH_2-CR_1)-$$
$$\quad\quad\quad |$$
$$\quad\quad(R_2)_m$$
$$\quad\quad\quad |$$
$$\quad\quad Si_nH_{2n+1}$$

wherein m is 0 or a positive integer of 1–20, n stands for 1, 2 or 3, $R_1$ means hydrogen, an alkyl group, an aryl group or a halogen, $R_2$ denotes an alkylene or phenylene group, and $R_1$ and $R_2$ may optionally contain one or more functional groups such as COOH, $NH_2$, Cl and OH.

BEST MODE FOR CARRYING OUT THE INVENTION

Figure 1:
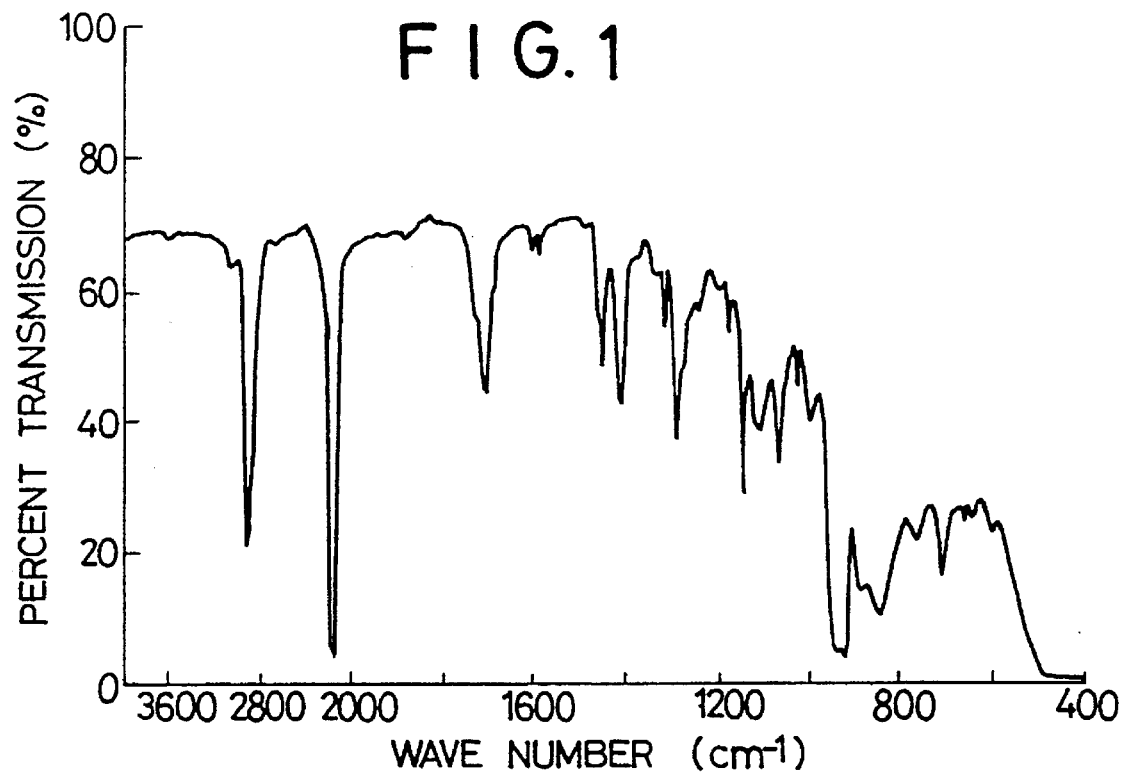
FIG. 1 is an infrared absorption spectrum of the silicon-containing polymer obtained in Example 11.

Reflecting the significant development of the semiconductor industry in recent years, $SiH_4$, $Si_2H_6$ and $Si_3H_8$ useful as raw materials in the present invention are produced in large volumes as gases for semiconductors and have recently become available at low prices industrially. As their preparation process, it has been known, for example, to reduce $SiCl_4$, $Si_2Cl_6$ and $Si_3Cl_8$ with a metal hydride or the like, to react a silicon alloy, which contains magnesium silicide as a principal component, with an acid as proposed by the present inventors (U.S. Pat. No. 4,610,859), or to subject trichlorosilane to disproportionation. In the present invention, the raw materials prepared in any one of these processes may be used suitably.

The other raw material is a compound having at least one carbon-carbon double bond (C=C) and/or at least one carbon-carbon triple bond (C≡C) per molecule, i.e., an alkene or alkyne, which may optionally contain one or more functional groups such as —COOH, —$NH_2$, —CHO, —C≡N, —NCO and/or

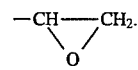

As specific examples, may be mentioned:

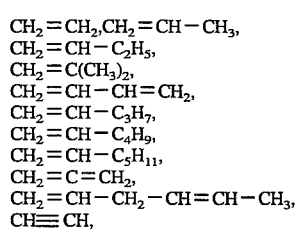

$CH_2=CH_2, CH_2=CH-CH_3,$
$CH_2=CH-C_2H_5,$
$CH_2=C(CH_3)_2,$
$CH_2=CH-CH=CH_2,$
$CH_2=CH-C_3H_7,$
$CH_2=CH-C_4H_9,$
$CH_2=CH-C_5H_{11},$
$CH_2=C=CH_2,$
$CH_2=CH-CH_2-CH=CH-CH_3,$
$CH≡CH,$

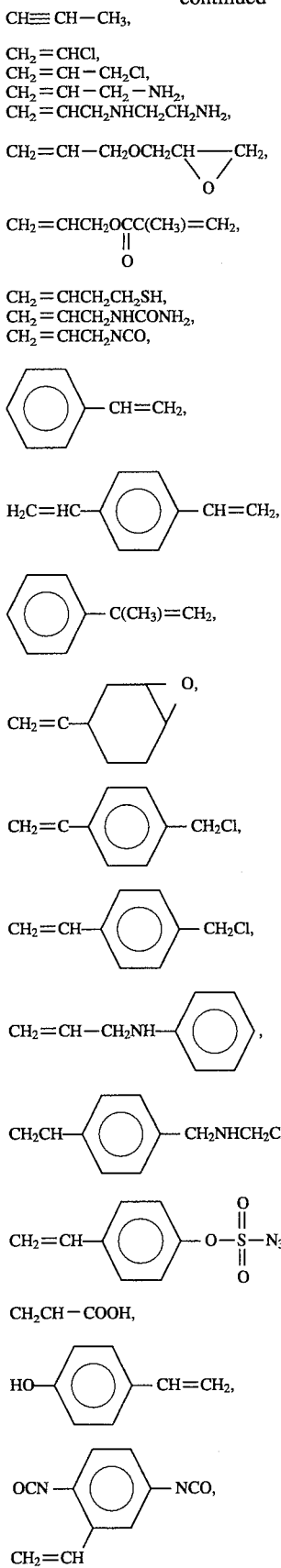

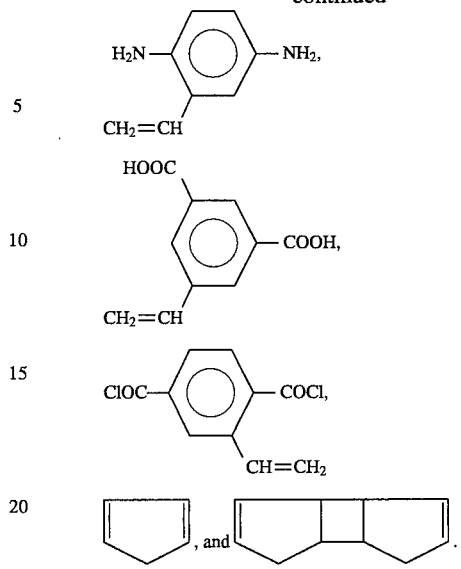

Two or more of these compounds may of course be used at the same time.

The catalyst useful in the practice of this invention is a catalyst composed of a metal of Group VIII, VIA, VIIA, VA, IVA or IIIA in the periodic table ["SHIN JIKKEN KAGAKU KOZA" (New Handbook of Laboratory Chemistry), The Maruzen Kabushiki Kaisha (1977)] or a catalyst containing a compound of the metal as a catalyst constituent. As such catalysts, may be mentioned metals, e.g., Fe, Co, Ni, Ru, Rh, Pd, Os, Ir, Pt, Cr, Mo, W, Mn, Tc, Re, Sc, Ti, V, Y, Zr, Nb, Hf, Ta, lantanides such as La and Ce, and actinides such as AC and Th; metal complexes such as $Fe(CO)_5$, $Co_2(CO)_3$, $L_2Ni(olefin)$, $L_2NiCl_2$, $RuCl_3$, $L_3RhCl$, $L_4Pd$, $L_2PdCl_2$, $IrCl_2$, $L_4Pt$, $[(olefin)PtCl_2]_2$ $H_2PtCl_6 \cdot 6H_2O$, $Ru(CO)_2$, $RuCl_2(P\phi_3)_3$, $Cr(CO)_6$, $Mn_2(CO)_{10}$, (wherein $\phi$ means phenyl and L stands for $PRh_3$ or $PR_3$), $(C_2H_5)_2TiCl_2$, $(C_2H_5)_2Ti(CH_3)_2$, $(C_2H_5)_2Ti(CH_2C_6H_5)_2$, $TiCl_4$, $Ti(OC_2H_5)_4$, $TiH_2$, $Ti(OC_4H_9)_2(CH_3COCHCOCH_3)_2$, $TiCl_3$, $TiO(CH_3COCHCOCH_3)_2$, $Ti(OCH(CH_3)_2)_4$, $(C_5H_5)_2ZrCl_2$, $(C_5H_5)_2Zr(CH_3)_2$, $ZrH_4$, $ZrCl_4$, $Zr(OC_2H_5)_4$, $Zr(CH_3COCHCOCH_3)_4$, $(C_5H_5)_2ZrH_2$, $(C_5H_5)_2ZrHCl$, $(C_5H_5)_2VCl_2$, $(C_5H_5)_2V(CH_3)_2$, $V(CH_3COCHCOCH_3)_3$, $(C_2H_5)V(CO)_4$, $V(CO)_6$, $VCl_3$, $VO(CH_3COCHCOCH_3)_2$, $Na(C_6H_{14}O_3)_2V(CO)_6$, $VOCl_3$, $TaCl_5$, $TaH$, $Ta(OCH_3)_4$, $Sm(OOCCH_3)_3 \cdot xH_2O$, $Sm(CH_3COCHCOCH_3)_3$, $SmCl_3$, $(C_2H_5)_2HfCl_2$, $CeCl_3$, $Ce(OOCCH_3)_3$, $Ce(CH_3COCHCOCH_3)_3 \cdot xH_2O$, $Y[CH_3COCH(OCH_3)]_3$, $YCl_3$, $Y(OOCC_{10}H_7)_3$, $Sc(OOCCH_3)_3 \cdot xH_2O$, $ScCl_3$, $Sc[OCH(CH_3)_2]_3$, $NbCl_5$, $Nb(OC_2H_5)_5$, $NbH_5$, $Th(CH_3COCHCOCH_3)_4$ and $ThCl_4$; metals carried on activated carbon or a metal oxide such as silica or alumina; and peroxides such as benzoyl peroxide.

These catalysts are either homogeneous or heterogeneous and most of them are sold in the market and are available readily. They may of course be synthesized with ease. The present invention makes use of the above-mentioned metal or its compound as an essential component of the catalyst. Needless to say, one or more other catalyst components may also be included in combination.

In the present invention, the reaction between $SiH_4$ and the aforementioned hydrocarbon is carried out at 0° C.–400° C. in the presence of such a catalyst as mentioned above.

No particular limitation is imposed on the above reaction except that the above-described reaction temperature and catalyst are used. The reaction may be conducted in either vapor phase or liquid phase.

The reaction temperature ranges from 0° C. to 400° C., preferably, from 50° C. to 200° C. and the catalyst may be either homogeneous or heterogeneous.

When the reaction is carried out in a vapor phase, the reaction may be conducted, for example, by bringing $SiH_4$ and a gaseous hydrocarbon such as alkene or alkane into contact with surfaces of a solid catalyst so as to react them there. When the reaction is performed in a liquid phase, the reaction may be conducted, for example, by blowing $SiH_4$ into a liquid hydrocarbon compound which contains a catalyst. In the latter case, may be used as a solvent an organic compound non-reactive with $SiH_4$ and the alkene or alkane compound, such as benzene, heptane, hexane or toluene. No particular limitation is imposed on the reaction pressure but a higher pressure is desirable from the standpoint of equilibrium. The reaction may be carried out in the concurrent presence of a gas such as hydrogen, argon, nitrogen or helium gas.

On the other hand, no specific limitation is imposed on the manner in which $Si_2H_6$ or $Si_3H_8$ is reacted with the aforementioned hydrocarbon. The reaction may be carried out in either vapor phase or liquid phase. The reaction may be performed in various ways. It may be mentioned by way of example that they are reacted under heat, under radiation of light, or in the presence of a catalyst.

Reaction conditions vary depending on the manner of the reaction. Regarding the reaction temperature for instance, it is desirable to conduct the reaction in a range of 50° C.–600° C., preferably, 200° C.–500° C. in the case of a thermal reaction; in a range of room temperature—200° C. in the case of an optical reaction; and in a range of 0° C.–300° C. in the case of a catalytic reaction. In the case of an optical reaction, ultraviolet rays of 2,500Å or shorter are effective for the efficient promotion of the reaction. In such an optical reaction, the existence of mercury may accelerate the reaction further since the mercury may act as a sensitizer. Among the reaction methods mentioned above, the catalytic reaction is most preferable. As to the specific manner for performing the catalytic reaction, it may be conducted in the same manner as in the case of $SiH_4$.

Reactions according to the present invention may be shown generally by the following equations:

$$SiH_4 + nCH_2=CH-R \rightarrow (R-CH_2-CH_2)_n SiH_{4-n}$$

$$SiH_4 + nCH_2 \equiv C-R \rightarrow (R-CH_2-CH_2)_n SiH_{4-n}$$

$$Si_2H_6 + aCH_2=CH-R \rightarrow R'_{3-j}H_j SiSiR'_{3-k}H_k$$

$$Si_3H_8 + bCH_2=CH-R \rightarrow R'_{3-l}H_l SiSi(R'_{2-m}) \cdot (H_m)SiR'_{3-n}H_n$$

$$Si_2H_6 + aCH_2 \equiv C-R \rightarrow R''_{3-j}H_j SiSiR''_{3-k}H_k$$

$$Si_3H_8 + bCH_2 \equiv C-R \rightarrow R''_{3-l}H_l SiSi(R''_{2-m}) \cdot (H_m)SiR''_{3-n}H_n$$

wherein R' means $-CH_2-CH_2-R$, R" denotes $-CH=CH-R$, a stands for 6-j-k, and b is 8-l-m-n. a, b and n may be controlled at will depending on reaction conditions such as reaction temperature, reaction pressure, reaction time, the kind of a catalyst, and the molar ratio of $SiH_4$, $Si_2H_6$ or $Si_3H_8$ to the hydrocarbon to be introduced.

As mentioned above, the reaction temperature may desirably be 0° C.–600° C. A higher reaction pressure is desirable from the viewpoint of the equilibrium of the reaction, and the reaction pressure may generally range from 0 to 1,000 atm, preferably, 0 to 100 atm. The molar ratio of the charge may be changed as desired in accordance with the kind of a target product. Although not limiting critically in particular, the ratio of the unsaturated hydrocarbon to $SiH_4$, $Si_2H_6$ or $Si_3H_8$ may generally range from 0.01 to 100. Further, the reaction time may be chosen at will from a range of several minutes—several hours.

Alkylsilanes and alkenylsilanes obtained in the above manner contain one or more highly-reactive Si—H bonds. By making use of the reactivity, their application as silicones, silane coupling agents, silylating agents and monomers for polymers is expected. They are novel organosilicon compounds which can contribute considerably to the development of functional materials.

There has not been any process for obtaining these compounds except the reduction of alkylchlorosilanes with an expensive reducing agent such as $LiAlH_4$, $NaAlH_4$ or $NaBH_4$. Accordingly, they have been extremely expensive and no substantial attempts have been made to develop their application fields. The present invention has solved such a drawback completely, thereby making it possible to produce functional monomers at low prices.

A description will next be made of the process for the preparation of the silicon-containing high molecular compound having recurring structural units represented by the following general formula:

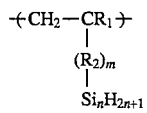

wherein m is 0 or a positive integer of 1–20, n stands for 1, 2 or 3, $R_1$ means hydrogen, an alkyl group, an aryl group or a halogen, $R_2$ denotes an alkylene or phenylene group, and $R_1$ and $R_2$ may optionally contain one or more functional groups such as COOH, $NH_2$, Cl and/or OH.

Where n stands for 1 and m is a positive integer of 5–20 or n stands for 1 or 3 and m is 0 or a positive integer of 1–20 in the above formula, the silicon-containing high molecular compound is a novel compound and has been proposed for the first time by the present invention. In the above formula, $R_1$ is hydrogen, a halogen, or preferably, the above-described group having 1–20 carbon atoms, for example,

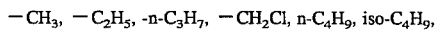

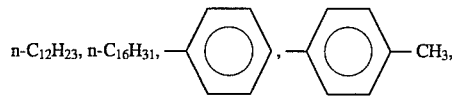

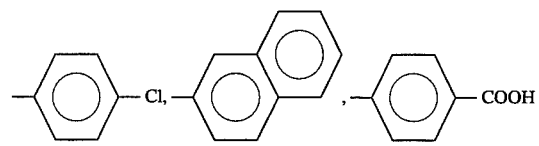

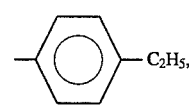

or the like. $R_2$ may preferably be the above-mentioned group having 1–20 carbon atoms, for example,

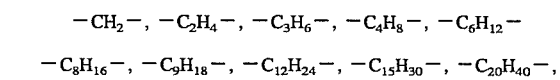

-continued

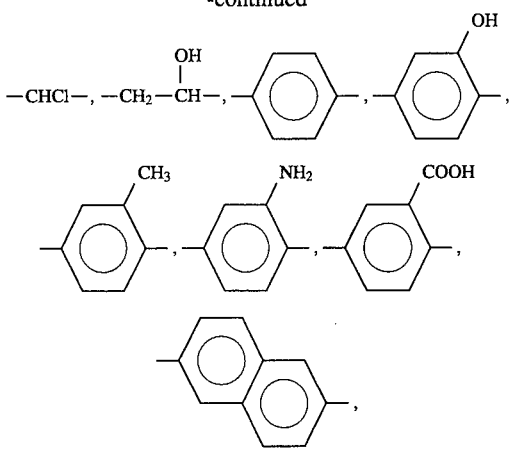

or the like.

The silicon-containing high molecular compound may be obtained, for example, by subjecting an α-olefin $CH_2=CR_1$ $[(R_2)_mSi_nH_{2n+1}]$ to anionic coordination polymerization, radical polymerization or ionic polymerization. Namely, its preparation may be achieved in various ways, for example, by subjecting the α-olefin to anionic coordination polymerization in the presence of a Ziegler-Natta catalyst (a catalyst composed of a salt of a transition metal such as titanium halide, vanadium halide or zirconium halide and an alkylaluminum); by subjecting the α-olefin to cationic polymerization in the presence of a catalyst such as metal oxide ($Cr_2O_3$, $SiO_2$, $Al_2O_3$ or the like), a hydroacid ($H_2SO_4$, $H_3PO_4$, $HClO_4$, HCl or the like), or Lewis acid ($BF_3$, $AlCl_3$, $FeCl_3$, $SnCl_4$, or the like); by subjecting the α-olefin to anionic polymerization in the presence of a catalyst such as alkali metal (Li, Na, K or the like), alkylalkali [$C_2H_5Na$, $(C_2H_5)_3Al$, $C_6H_5Li$ or the like], or hydroxide (NaOH, KOH, or the like); or by subjecting the α-olefin to radical polymerization in the presence of a peroxide as an initiator. Needless to say, the polymerization may be practised in either vapor phase or liquid phase and either with a solvent or without any solvent (bulk polymerization). In such polymerization, the molecular weight of the resulting polymer may be regulated easily with hydrogen or the like which is allowed to exist concurrently.

Describing the radical polymerization in further detail, no particular limitation is imposed on the manner of the radical polymerization and various methods may be adopted. For example, use of heat, light, radiation, electricity, catalyst (initiator) or the like is feasible. It is however most preferable to use a catalyst. As exemplary catalysts, may be mentioned hydrogen peroxide, ammonium persulfate, benzoyl peroxide, cumene peroxide, cyclohexane peroxide, di-t-butyl peroxide, t-butyl hydroperoxide, methyl ethyl ketone peroxide, azobisisobutylonitrile and the like.

In the above polymerization, it is also possible to additionally use dimethylaniline, Co or Mn naphthenate or the like as a cocatalyst (promoter); and/or sodium hyposulfite, sodium thiosulfate, mercaptan, ferrous ($Fe^{++}$) salt, cuprous ($Cu^+$) salt or the like as an activator (reducing agent).

For the control of the reaction velocity, it is possible to use mercaptan or its analogous compound or an aromatic nitro compound as a reaction decellerator. Mercaptan or its analogous compound may also be used as a polymerization degree regulator. A variety of crosslinking agents may also be used. Crosslinking may be effected as desired, for example, by copolymerization with a monomer such as $(CH_2=CH)_2SiH_2$ or $(CH_2=CH)_3SiH$.

No particular limitation is imposed on the manner of the polymerization. The polymerization may be performed in either vapor phase or liquid phase, and a polymerization method such as bulk polymerization, solution polymerization, suspension polymerization or emulsion polymerization may be used. The reaction temperature and reaction pressure vary depending on the manner of the polymerization and the monomers to be reacted. When a catalyst is used, the reaction temperature may be 0°–200° C., preferably, 20°–150° C. The higher the reaction pressure, the better from the standpoint of equilibrium. It may range from atmospheric pressure to 1,000 atm. It is also feasible to conduct the polymerization by using a solvent such as benzene, toluene, xylene, pentane, dimethylformamide, chloroform or water.

Regarding the radical polymerization in this invention, the structure of the polymer is not limited particularly. Its recurring units, molecular weight, molecular weight distribution, crosslinking degree and the like may vary depending on the kind of the monomer and the manner of polymerization. As the most representative polymer structure, the following recurring unit may be given by way of example.

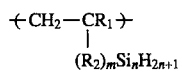

No limitation is imposed on the stereoregularity of the polymer. No particular limitation is imposed either on its molecular weight. However, about 100–10,000,000, preferably, about 200–1,000,000 is desirable in view of its shapability or moldability, its solubility in a solvent, etc.

Where n=1 in the silicon-containing high molecular compound, the radical polymerization may be carried out in the same manner as in the case of n=2 or 3.

Needless to say, polymerizable silicon compounds useful in the practice of this invention may be copolymerized (random, alternating, block, graft, or the like) with other polymerizable monomers, for example, ethylene, propylene, butene, butadiene, styrene, vinyl chloride, vinylidene chloride, acrylic esters, methyl methacrylate, vinyl acetate, acrylonitrile and ethylene tetrafluoride. The proportion of such a monomer may be chosen as desired depending on the purpose of use of the resulting copolymer. The unsaturated hydrocarbon may be used in a proportion of 0.00001–100,000 parts by weight, preferably, 0.001–1,000 parts by weight per part by weight of the silicon compound.

The silicon compound' usable as a monomer in the present invention is represented by the following general formula:

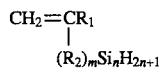

wherein m is 0 or a positive integer of 1–20, n stands for 1, 2 or 3, $R_1$ means hydrogen, an alkyl group, an aryl group or a halogen, for example, H, $CH_3$, $C_2H_5$, i-$C_3H_7$, φ (φ indicates a phenyl group. This definition will hereinafter be applied equally), φ$CH_3$, $CH_2$φ, F, Cl, Br or the like, $R_1$ having fewer carbon atoms is preferred and hydrogen is most preferable, $R_2$ denotes an alkylene or phenylene group, for example, $CH_2$, φ (φ indicates a phenylene group. This definition will hereinafter be applied equally. ), $CH_2$φ or the like, and $R_1$ and $R_2$ may optionally contain one or more functional groups such as COOH, $NH_2$, Cl and/or OH.

These monomers which contain one or more silyl groups and pertain to the present invention, namely, the silicon compounds may be prepared by various processes. Although not limiting particularly, processes such as those to be described by the following equations may be employed in the present invention by way of example.

$$\text{HSiCl}_3 + \text{ClH}_2\text{C}(\text{CH}_2)_n\text{CH}=\text{CH}_2 \xrightarrow[600°\text{ C.}]{-\text{HCl}} \quad (1)$$

$$\text{Cl}_3\text{Si}(\text{CH}_2)_{n+1}\text{CH}=\text{CH}_2 \xrightarrow{\text{LiAlH}_4}$$

$$\text{H}_3\text{Si}(\text{CH}_2)_{n+1}\text{CH}=\text{CH}_2$$

$$\text{HSiCl}_3 + \text{H}_3\text{C}(\text{CH}_2)_n\text{CH}=\text{CH}_2 \xrightarrow[-\text{H}_2]{\text{BCl}_3,\ 300°\text{ C.}} \quad (2)$$

$$\text{Cl}_3\text{Si}(\text{CH}_2)_{n+1}\text{CH}=\text{CH}_2 \xrightarrow{\text{LiAlH}_4}$$

$$\text{H}_3\text{Si}(\text{CH}_2)_{n+1}\text{CH}=\text{CH}_2$$

$$\text{SiH}_4 + \text{CH}_2=\text{CH}(\text{CH}_2)_n\text{CH}=\text{CH}_2 \xrightarrow{\text{Pt, 200° C.}} \quad (3)$$

$$\text{H}_3\text{Si}(\text{CH}_2)_{n+2}\text{CH}=\text{CH}_2$$

$$\text{SiH}_4 + \text{CH}\equiv\text{CH} \xrightarrow{\text{Pt, 200° C.}} \text{H}_3\text{SiCH}=\text{CH}_2 \quad (4)$$

$$\text{SiH}_4 + \text{ClH}_2\text{C}(\text{CH}_2)_n\text{CH}=\text{CH}_2 \xrightarrow{-\text{HCl}} \quad (5)$$

$$\text{H}_3\text{Si}(\text{CH}_2)_{n+1}\text{CH}=\text{CH}_2$$

$$\text{SiH}_4 + \text{H}_3\text{C}(\text{CH}_2)_n\text{CH}=\text{CH}_2 \xrightarrow{-\text{H}_2} \quad (6)$$

$$\text{H}_3\text{Si}(\text{CH}_2)_{n+1}\text{CH}=\text{CH}_2$$

Among the above processes, the processes (3), (4), (5) and (6) use $\text{SiH}_4$ as a starting material and especially, the processes (3) and (4) are hydrosilylating reactions in which the Group VIII metal is used as a catalyst as described above. These processes can easily provide desired α-olefins containing one or more $\text{SiH}_3$ groups. In recent years, $\text{SiH}_4$ is a new silicon-containing raw material whose demand has increased for polysilicon and amorphous silicon. It is now produced in a large volume and at a low price. This trend is expected to be enhanced further in the future (this also applies to. $\text{Si}_2\text{H}_6$ and $\text{Si}_3\text{H}_8$). Two or more of these silicon compounds may be used in combination.

The silicon-containing polymers according to the present invention are easy not only in their preparation but also in changing their processability (flow characteristics of their melts, their solubility in solvents) by controlling the type of the polymer or copolymer (random, block, alternating or graft) and/or the monomer composition, molecular weight and stereoregularity of the copolymer. In addition, the $\text{SiH}_3$ groups contained in the silicon-containing polymers of this invention are relatively stable, and even when placed in air, they are not oxidized easily at room temperature and may be oxidized barely at temperatures as high as about 100°–200° C.

The silicon-containing polymers according to the present invention are soluble in solvents and are thermoplastic. Their industrial utility is therefore great, and numerous application fields are expected for them, e.g., prepolymers for ceramics (SIC), binders for ceramics, surface treatment agents, water repellants, raw materials for IPN, semiconductors, photoresists, etc. Functions of these polymers make use of the high reactivity of Si—H bond and the electrical conductivity and optical splittability of Si—Si bond. Especially, the function employed favorably in the present invention resides in the reactivity of silyl group ($\text{SiH}_3$). It is possible to incorporate an interesting function in conventional polymers such as polystyrene, polyvinyl chloride and polymethacrylic acid, for example, to impart crosslinkability, foamability, or reactivity with other monomer or polymer by taking the silicon compound partly in the polymers through copolymerization. Namely, the present invention can contribute greatly to the creation of new high functional materials which have not existed so far.

A description will next be made of the process for the production of silicon carbide by firing the silicon-containing high molecular compound at elevated temperatures (converting the compound into ceramics).

The conversion of the silicon-containing compound of this invention into ceramics may be carried out basically in the same manner as in the use of conventional silicon-containing prepolymers, for example, a prepolymer having the following recurring units:

or

The manner of conversion into ceramics will hereinafter be described in detail.

A first method comprises applying an ordinary resin processing technique, such as injection molding or extrusion forming, to the silicon-containing high molecular compound of this invention in an inert gas like conventional thermoplastic polymers by making use of the high processability of the silicon-containing high molecular compound, thereby to shape the compound into a desired shape and then firing the thus-shaped body at an elevated temperature (500°–2,500° C.).

Ceramics such as SiC and $\text{Si}_3\text{N}_4$ require a large and expensive compression molding machine due to the adoption of such a shaping method that powder is generally compression-molded at an extremely high pressure (for example, an elevated pressure as high as 1,000 atm or even higher) and then sintered at a high temperature. In addition, products of complex configurations cannot be obtained due to the use of compression molding. The above method can solve such problems. Incidentally, it is of course possible to perform compression molding as in the conventional methods after the silicon-containing high molecular compound is fired into SiC powder at a high temperature.

Similarly to the first method, a second method can also reduce the drawbacks of conventional compression molding methods of ceramic powder. In the second method, ceramics powder such as SiC powder or $\text{Si}_3\text{N}_4$ powder is added to an extent not losing its processability. Like the first method, it is then injection-molded or extrusion-formed, followed by firing at elevated temperatures (in this method, the thus-added SiC powder is expected to act like a binder and such an action is also expected to be shown by the silicon-containing high molecular compound containing a small amount of Si).

Processes have conventionally been developed that ceramics powder and an additive such as easily-processable organic compound are mixed and after injection molding of the resultant mixture, the thus-molded green body is sintered at elevated temperatures (including elimination of the additive and presintering). Organic additives reported in the past include primarily mixtures obtained respectively by mixing lubricants such as polystyrene, styrene-butadiene copolymer and stearic acid with a plasticizer more susceptible to decomposition and evaporation such as diethyl phthalate at suitable ratios, those prepared by adding a thermosetting resin (phenol resin) to the former, those formed by mixing wax in thermosetting resins (phenol resins, epoxy resins, coumaron-indene resins), mixtures of monoolefin polymers and ethylene glycol, compositions composed principally of sublimable substances such as naphthalene, etc. The most serious problem in the present injecting molding processes resides in that there is a limitation to the strength of molded or otherwise shaped products for the formation of pores in the ceramics in the additive (resin) elimination step and other reasons.

In the case of the silicon-containing high molecular compound according to this invention on the other hand, a majority of the polymer is allowed to remain as SiC in the ceramics as compared with the above-mentioned additives. Fewer pores are hence formed in the ceramics, so that a greater bulk density is achieved. Furthermore, the silicon-containing high molecular compound acts like a binder so that molded products have high strength.

The process essentially comprises a first step of mixing and kneading SiC or $Si_3N_4$ powder with the silicon-containing high molecular compound as an additive, a second step of forming the resultant mixture, and a third step of sintering the thus-formed green body (including elimination of the additive and presintering).

In the first step, the ceramics powder and the silicon-containing high molecular compound are mixed. Here, it is possible to use two or more silicon-containing high molecular compounds. It is also possible to employ one or more silicon-free other additives (thermoplastic resins, plasticizers, lubricants, aids) at the same time as described above. The amount of the silicon-containing high molecular compound to be added varies depending on its kind, other additive or additives to be employed simultaneously and the subsequent molding or forming method but may preferably be 0.01 wt. %–200 wt. % with 0.1 wt. %–50 wt. % being more preferred. If it is added in an unduly small amount, it is difficult to obtain a molded or otherwise shaped, sintered SiC body. If it is added too much on the contrary, the strength is reduced and the high-temperature oxidation resistance is also lowered.

The second step comprises the forming of the mixture. There are various methods, for example, including mechanical pressing, isostatic pressing, slip casting, doctor-blade forming, extrusion forming, injection molding, hot pressing, etc. These methods can all be employed. Among these, injection molding allows the exhibition of the effects of this invention to the greatest extent. Hot pressing and isostatic pressing can simultaneously effect sintering which will be described next.

The third step is a sintering step of a formed or molded green body. It may be required to conduct elimination of additives (degreasing, binder removal, dewaxing) and presintering as pre-steps if necessary. The temperature of such pre-steps may generally range from room temperature to 500° C. The final sintering is practised in a temperature range of 500°–2,500° C.

The third process is useful in producing fibrous ceramics by spinning the silicon-containing high molecular compound into a fibrous shape like SiC fibers and then firing the thus-spun green fibers.

In the present invention, the formation of the silicon-containing high molecular compound into fibers may be conducted basically in the same manner as the use of conventional polycarbosilanes, polysilastyrenes and the like, for example, prepolymers containing

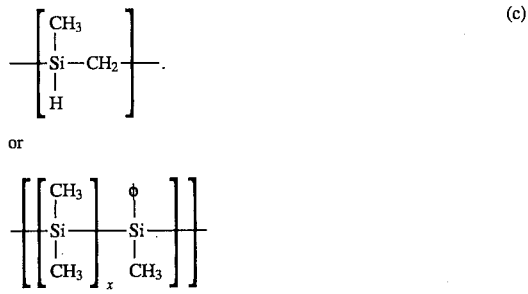

as recurring structural units.

Namely, the silicon-containing high molecular compound of this invention is spun in an inert gas in accordance with any one of melt spinning, wet spinning and dry spinning methods, most preferably, a melt or dry spinning method by making use of the easy processability of the compound.

The thus-obtained fibers are then subjected to surface oxidation or infusibilizing treatment in a temperature range of about 50°–300° C. in an oxygen-containing gas so as to prevent cohesion of the fibers. The treatment time varies depending on the temperature and the concentration of oxygen, but may be suitable from a range of from several seconds to several hours. The concentration of oxygen may range from 10 ppm to 100%. It is of course possible to omit this treatment depending on the nature of fibers as will be demonstrated in subsequent Examples.

The fibers thus infusibilized are thereafter heated at about 800°–2,000° C. for several minutes to several tens hours in vacuo or in an atmosphere of an inert gas such as nitrogen, helium, neon, argon or krypton, thereby to form desired silicon carbide fibers. As merits of the process of this invention for the preparation of silicon carbide fibers, may be mentioned that as will be described in the subsequent Examples, the yield of the ceramics(SiC) is extremely high and that the fibers contain extremely little free carbon after their firing.

For example, a polycarbosilane composed of the following recurring units:

is now used as a prepolymer for SiC fibers. Although the yield of the ceramics when formed into fibers is rather good, they are said to contain a lot of free carbon (about 10 wt. %). When employed as fibers, $SiO_2$ is said to mix in (to about 20 wt. %) during the infusibilizing treatment applied in the course of the spinning step. They are considered to give deleterious effects to the strength of fibers.

The process of this invention for the production of silicon carbide fibers by firing the silicon-containing high molecular compound permits suitable oxidation and infusibilization of the surfaces of the spun polymer by controlling the amount of oxygen (oxygen concentration) in an oxygen-containing gaseous atmosphere in which the infusibilization treatment is applied, and the temperature for the infusibilization treatment, because the silicon-containing high molecular compound contains silyl groups ($SiH_3$ groups) having high reactivity with oxygen. Namely, in the process of this invention, some Si—H bonds of silyl groups ($SiH_3$ groups) on the surface are oxidized and crosslinked by siloxane bonds. It is hence possible to obtain fibers of high properties, i.e., containing less incorporated oxygen and less silica compared with the use of a conventional polycarbosilane.

As a further feature of the silicon-containing high molecular compounds according to the present invention, the infusibilization treatment may be carried out with a nitrogen-containing compound by making use of the fact that silyl groups are highly reactive with N-H bonds. The term "nitrogen-containing compound" as used herein means at least one N—H bond per molecule. Specifically, it includes

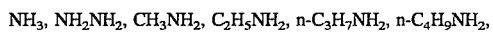

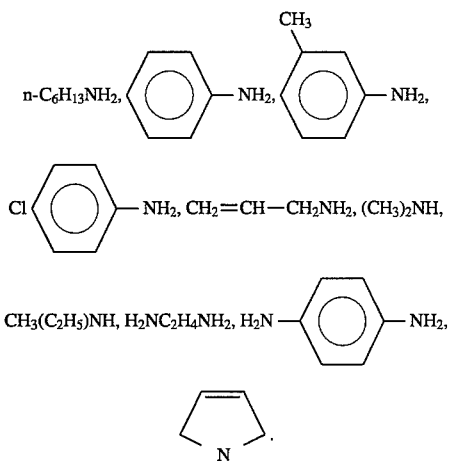

Among them, those having a lower boiling point and fewer carbon atoms are desirable. Specific examples include $NH_3$, $NH_2NH_2$, $CH_3NH_2$, $C_2H_5NH_2$, $(CH_3)_2NH$, etc. In this invention, no particular limitation is imposed on the manner of the infusibilization treatment. It may be carried out in either liquid or vapor phase.

When it is desired to effect the infusibilization treatment in a liquid phase, for example, spun fibers may be immersed for a predetermined period of time in a solution of the above-mentioned nitrogen-containing compound. In this case, it is possible to use benzene, toluene, xylene, hexane, heptane, ether, dioxane or the like as a solvent and an alkali metal or an alkali metal amide as a catalyst. The reaction temperature may preferably range from 0° to 200° C. in general. The treatment time varies depending on the reaction time, but may generally range from several tens seconds to several hours. When it is desired to conduct the infusibilization treatment in a vapor phase on the other hand, it is desirable to use as the nitrogen-containing compound a low boiling-point compound such as $NH_3$, $CH_3NH_2$ or $C_2H_5NH_2$. The reaction temperature may generally range from 0° C. to 500° C., with a range of 50°–400° C. being preferred. The treatment time varies depending on the reaction temperature as mentioned above. It is also possible to use a catalyst. Needless to say, the amount of remaining $SiO_2$ can be reduced significantly by the above infusibilization treatment which makes use of the nitrogen-containing compound.

It is also feasible to conduct the infusibilization treatment in the presence of an alkali catalyst in water or an alcohol by making use of the fact that silyl groups are susceptible to splitting in an alkaline atmosphere.

Reflecting the low carbon and silica contents of silicon carbide fibers according to this invention, they have much superior high-temperature strength to fibers obtained by conventional processes as will be demonstrated in Examples.

The fourth process comprises impregnating a sintered body of a silicon-containing ceramic material such as SiC or $Si_3N_4$ with a solution of the silicon-containing high molecular compound of this invention and then firing the thus-impregnated sintered body. By this process, the mechanical strength of the sintered ceramic body is enhanced. This process is particularly effective in improving the mechanical strength of a sintered body which has been obtained in accordance with the first or second process described above and contain pores therein.

It is the fundamental feature of the present invention that the high molecular organosilicon compound is fired at a high temperature to produce SiC. This invention is therefore not necessarily limited to the first—fourth processes described above.

Incidentally, it is not clear why the yield of the ceramics is high and less free carbon is contained in fibers in the process of the present invention. The Si—H bonds of $SiH_3$ groups seem to be split first to induce crosslinking in the course of the pyrolysis, thereby making the starting material difficult to scatter out of the system, and the thus-released hydrogen appears to prevent the carbonization of the resulting polymer.

This invention will hereinafter be described by the following Examples.

EXAMPLE 1

Fourteen millimoles of $SiH_4$, 42 mmol of 1,5-hexadiene and as a catalyst, 0.047 mmol of $Pt(P\phi_3)_4$ were charged in a 50-ml autoclave, followed by reaction at 80° C. for 3 hours under stirring. After completion of the reaction, the reaction mixture was analyzed by gas chromatography.

The reaction mixture was found to contain the following products:

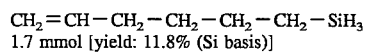
1.7 mmol [yield: 11.8% (Si basis)]

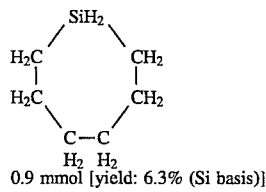
0.9 mmol [yield: 6.3% (Si basis)]

Trace amounts of other products were also observed.

EXAMPLE 2

Fifty-three millimoles of $SiH_4$, 160 mmol of 1-hexene and as a catalyst, 0.020 mmol of $Pt(P\phi_3)_4$ were charged in a 50-ml autoclave, followed by reaction at 80° C. for 20 hours under stirring. After completion of the reaction, the reaction mixture was analyzed by gas chromatography.

The reaction mixture was found to contain the following products:

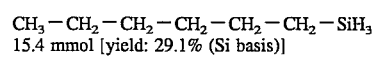
15.4 mmol [yield: 29.1% (Si basis)]

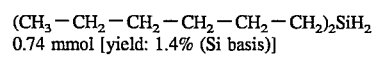
0.74 mmol [yield: 1.4% (Si basis)]

Trace amounts of other products were also observed.

EXAMPLE 3

An experiment was conducted in the same manner as in Example 2 except that activated carbon with 5 wt. % of Pt carried thereon was used as a catalyst in an amount of 0.019 mmol (in terms of Pt).

The reaction mixture was found to contain the following products:

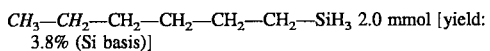
$CH_3$—$CH_2$—$CH_2$—$CH_2$—$CH_2$—$CH_2$—$SiH_3$ 2.0 mmol [yield: 3.8% (Si basis)]

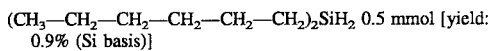
$(CH_3$—$CH_2$—$CH_2$—$CH_2$—$CH_2$—$CH_2)_2SiH_2$ 0.5 mmol [yield: 0.9% (Si basis)]

Trace amounts of other products were also observed.

EXAMPLE 4

An experiment was conducted in the same manner as in Example 1 except for the use of 0.28 mmol of $Mo(CO)_6$ as a catalyst.

The reaction mixture was found to contain the following products:

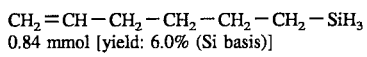
$CH_2=CH-CH_2-CH_2-CH_2-CH_2-SiH_3$
0.84 mmol [yield: 6.0% (Si basis)]

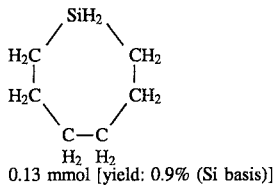
0.13 mmol [yield: 0.9% (Si basis)]

EXAMPLE 5

An experiment was conducted in the same manner as in Example 1 except for the use of 0.28 mmol of $V(acac)_3$ (acac: acetyl acetate) as a catalyst.

The reaction mixture was found to contain the following product:

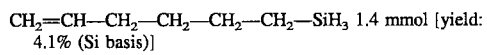
$CH_2=CH$—$CH_2$—$CH_2$—$CH_2$—$CH_2$—$SiH_3$ 1.4 mmol [yield: 4.1% (Si basis)]

Trace amounts of other products were also observed.

EXAMPLE 6

Forty millimoles of $SiH_4$, 180 mmol of acetylene and as a catalyst, 1.6 g of activated carbon with 0.5 wt. % of Pt carried thereon were charged in a 2-l autoclave, followed by reaction at 100° C. for 6 hours under stirring. After completion of the reaction, vapor-phase components were analyzed as is to analyze volatile compounds while non-volatile components were analyzed as a toluene solution, both, by gas chromatography.

The reaction mixture was found to contain the following products:

$CH_2=CH$—$SiH_3$ 13.2 mmol [yield: 33% (Si basis)]

$(CH_2=CH)_2SiH_2$ 9.2 mmol (yield: 23%)

$H_3Si$—$CH_2$—$CH_2$—$SiH_3$ 0.8 mmol (yield: 4%)

Trace amounts of other products were also observed.

EXAMPLE 7

Forty millimoles of $SiH_4$, 180 mmol of acetylene and as a catalyst, 0.4 g of $(C_6H_5)_2Ti(CH_2C_6H_5)_2$ were charged in a 2-l autoclave, followed by reaction at 150° C. for 3 hours under stirring. After completion of the reaction, vapor-phase components were analyzed as is to analyze volatile compounds while non-volatile components were analyzed as a toluene solution, both, by gas chromatography.

The reaction mixture was found to contain the following products:

$CH_2=CH$—$SiH_3$ 1.7 mmol [yield: 4.3% (Si basis)]

$(CH_2=CH)_2SiH_2$ 0.8 mmol (2.0%)

$H_3Si$—$CH_2$—$CH_2$—$SiH_3$ 0.1 mmol (0.5%)

Other products were also observed.

EXAMPLE 8

Fifty millimoles of $Si_2H_6$, 170 mmol of acetylene and as a catalyst, 1.7 g of activated carbon with 0.6 wt. % of Pt carried thereon were charged in a 2-l autoclave, followed by reaction at 100° C. for 5 hours under stirring. After completion of the reaction, vapor-phase components were analyzed as is to analyze volatile compounds while non-volatile components were analyzed as a toluene solution, both, by gas chromatography.

The reaction mixture was found to contain the following products:

$CH_2=CH$—$Si_2H_5$ 6.0 mmol [yield: 12% (Si basis)]

$CH_2CH$—$Si(H_2)Si(CH_2=CH)H_2$ 15.5 mmol [yield: 31% (Si basis)]

$(CH_2=CH)_2Si(H)SiH_3$ 2.5 mmol [yield: 5% (Si basis)]

$H_5Si_2$—$CH_2$—$CH_2$—$Si_2H_5$ 1.0 mmol [yield: 2% (Si basis)]

Small amounts of other products were also observed,

EXAMPLE 9

After charging 1,000 mmol of propylene, 200 ml of heptane and 0.5 g of $RuCl_2(P\phi_3)_3$ as a catalyst in a 500-ml autoclave, the temperature was raised to 80° C., and 70 mmol of $Si_2H_6$ were then charged into the autoclave over 5 hours. After completion of the reaction, the analysis of vapor-phase and liquid-phase components was conducted by gas chromatography.

The reaction mixture was found to contain the following products:

$CH_2CH_2CH_2Si_2H_5$ 4.2 mmol [yield: 6% (Si basis)]

$CH_3CH_2CH_2Si(H_2)Si(CH_2CH_2CH_3)H_2$ 23.8 mmol [yield: 34% (Si basis)]

$(CH_3CH_2CH_2)_2Si(H)SiH_3$ 5.6 mmol [yield: 8% (Si basis)]

$H_5Si_2CH_2$—$CH_2$—$Si_2H_5$ 0.4 mmol [yield: 1% (Si basis)]

Small amounts of other products were also observed.

EXAMPLE 10

After charging 850 mmol of 1,3-butadiene, 200 ml of xylene and 0.5 g of $Pt(P\phi_3)_4$ as a catalyst in a 500-ml autoclave, the temperature was raised to 100° C., and 40 mmol of $Si_3H_8$ were then charged into the autoclave over 5 hours. After completion of the reaction, the analysis of vapor-phase and liquid-phase components was conducted by gas chromatography.

The reaction mixture was found to contain the following products:

R'Si$_3$H$_7$ 4.2 mmol [yield: 10% (Si basis)]

R'(H$_2$)SiSi(H$_2$)Si(R')H$_2$ 4.8 mmol [yield: 12% (Si basis)]

R'$_2$(H)SiSi$_2$H$_5$ 2.8 mmol [yield: 7% (Si basis)]

(R' means 1-butenyl or 2-butenyl group).

In addition, some unidentifiable high b.p. byproducts were also observed.

EXAMPLE 11

In an autoclave whose capacity was 100 ml, were charged 14.2 g (260 mmol) of vinylsilane (CH$_2$=CH—SiH$_3$, b.p. −23° C.) and 1.0 g of benzoyl peroxide as a polymerization initiator, followed by reaction at 80° C. for 8 hours.

After completion of the reaction, the autoclave was opened to obtain 13.6 g of a viscous product (yield: 96%). The viscosity of the product was 2.3 cps at 20° C. As a result of its analysis by liquid chromatography, it has a molecular weight range of about 4,000–15,000 (in terms of polystyrene). An IR analysis indicated an absorption peak characteristic to SiH$_3$ groups (FIG. 1).

EXAMPLE 12

An experiment was conducted in the same manner as in Example 11 except that 0.5 g of azobisisobutyronitrile (AIBN) was used as a polymerization initiator.

Figure 2:
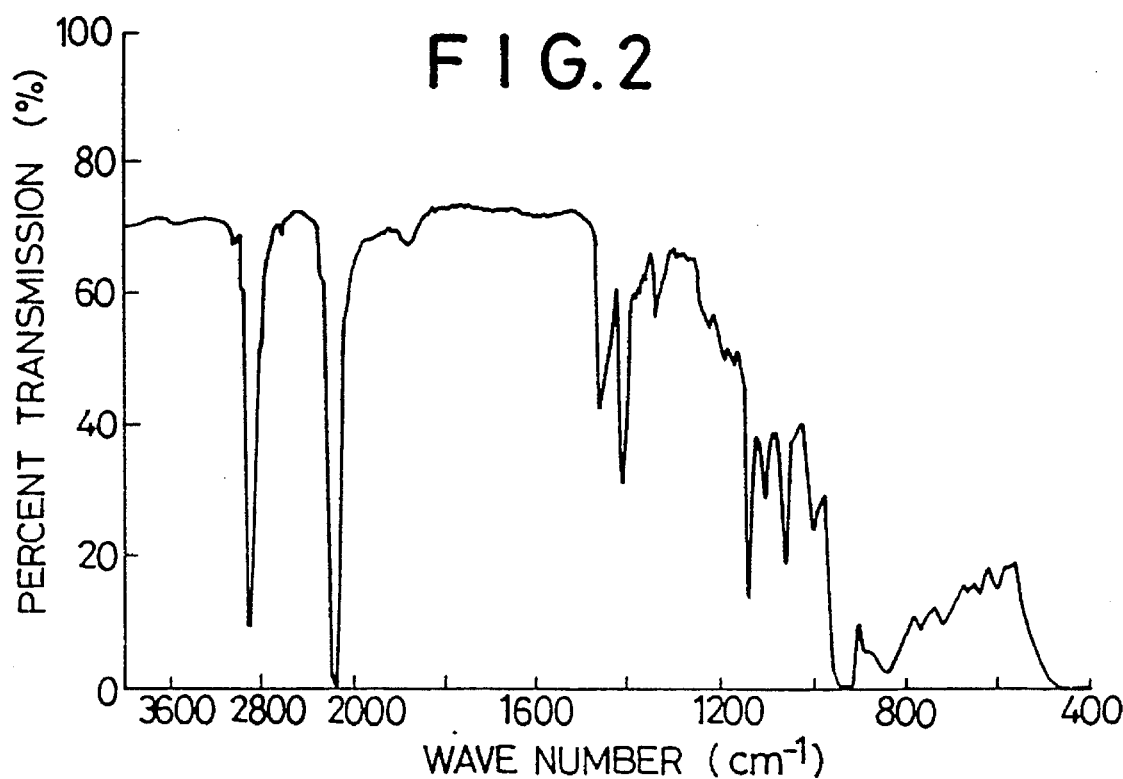
FIG. 2 is an infrared absorption spectrum of the silicon-containing polymer obtained in Example 12.

The resultant product was 13.1 g heavy (yield: 92%), and the viscosity of the product was 2.5 cps at 20° C. As a result of its analysis by liquid chromatography, it had a molecular weight range of about 5,000–17,000. An IR analysis indicated an absorption peak characteristic to SiH$_3$ groups (FIG. 2).

EXAMPLE 13

An experiment was conducted in the same manner as in Example 11 except that 21.4 g (177 mmol) of 2-chloro-4-silyl-1-butene (CH$_2$=CCl—CH$_2$—CH$_2$—SiH$_3$) was used in place of vinylsilane.

The resultant product was 9.8 g heavy (yield: 46%), and the viscosity of the product was 1.9 cps at 20° C. As a result of its analysis by liquid chromatography, it had a molecular weight range of about 1,000–10,000.

EXAMPLE 14

Charged in a 100-ml autoclave were 15.1 g 260 mmol) of vinylsilane (CH$_2$=CH—SiH$_3$, b.p. −23° C.) and 31.2 g (300 mmol) of styrene, followed by further charging of 1.2 of benzoyl peroxide as a polymerization initiator. Under hermetic condition, they were reacted at 80° C. for 8 hours.

After completion of the reaction, the autoclave was opened and its contents were poured into methanol under stirring. The resultant polymer was in the form of white powder and its weight was 39.8 g. The Si content of the polymer was 15 wt. %. The polymer had a molecular weight range of about 5,000–15,000.

EXAMPLE 15

Charged in a 500-ml autoclave were 300 ml of water containing 0.3 g of polyvinyl alcohol dissolved therein, 0.2 g of lauroyl peroxide, 50 g of vinylsilane and 100 g of vinyl chloride. Under hermetic condition, they were reacted at 60° C. for 8 hours.

After completion of the reaction, the autoclave was opened, and the resultant white powder was washed with water and then dried. The thus-obtained polymer was 125 g heavy and had an Si content of 17 wt. %. The polymer had a molecular weight range of about 5,000–15,000.

EXAMPLE 16

Charged in a 100-ml autoclave were 24.2 g 200 mmol) of 2-chloro-4-silyl-1-butene (CH$_2$=CCl—CH$_2$—CH$_2$—SiH$_3$), 31.2 g (300 mmol) of styrene and 0.5 g of AIBN (azobisisobutyronitrile) as a polymerization initiator, followed by reaction at 80° C. for 8 hours under hermetic condition.

After completion of the reaction, the autoclave was opened and its contents were poured into methanol under stirring. The resultant polymer was in the form of white powder and its weight was 33.2 g. The Si content of the polymer was 16 wt. %. The polymer had a molecular weight range of about 3,000–10,000.

EXAMPLE 17

CH$_2$=CH—SiCl$_3$ was reduced with LiAlH$_4$ to obtain CH$_2$=CH—SiH$_3$. In a nitrogen atmosphere, 36.7 g of the vinylsilane, 1 g of a titanium trichloride base catalyst for the polymerization of olefins (product of Toho Titanium Company, Limited), 3.3 ml of Al(i-C$_4$H$_9$)$_3$ and 150 ml of n-heptane were charged in an autoclave whose capacity was 200-ml. They were reacted at 70° C. for 4 hours. After completion of the reaction, the reaction mixture was added to methanol, thereby removing catalyst residue from the resultant polymer and at the same time causing the polymer to crystalize out. The thus-obtained polymer was 19 g heavy. As a result of its IR, elemental analysis and the like, it was confirmed to be a polymer having the following recurring structural units:

(a) 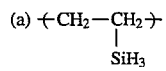

The polymer was stable at room temperature in air. At about 150° C., SiH$_3$ groups were lost suddenly, and siloxane bonds were formed. The degree of its crystallinity was about 60% and its melting point was 170°–180° C. Its average molecular weight was about 100,000 (by the viscosity method; each subsequent average molecular weight will be by the same method).

Evaluation results of the polymer are shown in Table 1.

Next, 0.5 g of the above polymer was placed in a silica-made firing tube whose inner diameter was 15 mm. In an argon stream (flow velocity: 50 ml/min), it was heated to 1,400° C. at a heating rate of 5° C./min. The yield of the resultant ceramics was 55 wt. % (79% on Si basis). The thus-fired product was fired further to 2,000° C. and was then analyzed by X-ray diffractometry. No diffraction peak characteristic to free carbon was observed.

EXAMPLE 18

An experiment was conducted in the same manner as in Example 17 except that the heating rate was changed to 0.5° C./min upon firing the polymer.

Results are also given in Table 1.

EXAMPLE 19

In an autoclave whose capacity was 100 ml, were charged 14.2 g (260 mmol) of vinylsilane ($CH_2=CH-SiH_3$, b.p. −23° C.) and 1.0 g of benzoyl peroxide as a polymerization initiator, followed by reaction at 80° C. for 8 hours.

After completion of the reaction, the autoclave was opened to obtain 13.6 g of a viscous product [polyvinylsilane (b)] (yield: 96%). The viscosity of the product was 2.3 cps at 20° C. As a result of its analysis by liquid chromatography, it had a molecular weight of about 3,000 (in terms of polystyrene). An IR analysis indicated an absorption peak characteristic to $SiH_3$ groups. The polymer was evaluated in the same manner as in Example 17.

Evaluation results of the polymer are shown in Table 1.

EXAMPLES 20 & 21

Experiments were separately carried out in the same manner as in Example 17 except that propylsilane and butenylsilane were used respectively as polymerization monomers in place of vinylsilane, thereby obtaining polymers having the following recurring structural units:

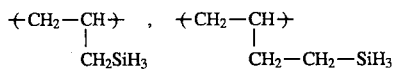

respectively.

Evaluation results of the polymer are shown in Table 1.

EXAMPLE 22

Polyvinyldisilane was obtained by using vinyldisilane as a monomer in Example 17. The polymer was fired in the same manner as in Example 17.

Evaluation results are shown in Table 1.

COMPARATIVE EXAMPLES 1 & 2

Polymer evaluation was conducted in the same manner as in Example 17 except that permethylpolysilane (product of Shin Nisso Kako Co., Ltd.; average molecular weight: about 2,000) having the following recurring units:

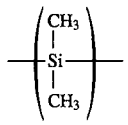

and polycarboxysilane having the following recurring units:

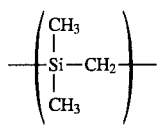

(which had been obtained by heating and firing permethylpolysilane at 400° C. and 100 atm in an autoclave) were used separately as polymers.

Results are given in Table 1.

EXAMPLE 23

Charged in an autoclave were 100 g of vinyl-silane and 1 g of AIBN (azobisisobutyronitrile), followed by polymerization at 70° C. for 8 hours to obtain about 90 g of a silicon-containing oily polymer (c) having an average molecular weight of about 2,000.

Forty grams of commercial SiC powder of about 300 mesh on average and 5 g of the above polymer (c) were mixed and kneaded, and then compression-molded into a crucible-like shape. The compression-molded body was then heated in a vacuum while raising the temperature from room temperature to 1,500° C., followed by firing at 1,800° C. for 4 hours.

The bulk specific gravity of the resultant crucible was 3.12. When the crucible was used for melting polycrystalline silicon, the crucible had a service life improved significantly compared with conventional SiC crucibles. Moreover, single crystals obtained by the pulling method contained extremely little impurities.

EXAMPLE 24

After mixing 6 g of the silicon-containing polymer (c) and 25 g of polystyrene with 40 g of SiC powder of the same kind as that employed in Example 23, the resultant mixture was heated and formed into a rod-like shape at 150° C. in nitrogen gas. The rod-like green body was heated gradually from room temperature to 600° C. under reduced pressure, followed by firing at 1,700° C. for 5 hours in an argon atmosphere.

The bulk specific gravity of the thus-obtained sintered body was 3.04. When the rod-like sintered body was used as a heating element, it fully withstood the actual use and compared with conventional SiC heating elements, had a longer service life.

EXAMPLE 25

Two hundred grams of vinylsilane were polymerized at 70° C. for 3 hours by using a titanium trichloride base catalyst for the polymerization of olefins, thereby obtaining 110 g of powdery polyvinylsilane (d).

After mixing 10 g of the polyvinylsilane (d) with 40 g of SiC powder of the same kind as that employed in Example 23, the resultant mixture was formed into a rod-like shape under a pressure of 200 Kg/cm². The rod-like green body was heated gradually from room temperature to 1,700° C. under reduced pressure, followed by firing at 1,700° C. for 5 hours in an argon atmosphere.

The bulk specific gravity of the thus-obtained sintered body was 3.04. When the rod-like sintered body was used as a heating element, it fully withstood the actual use and compared with conventional SiC heating elements, had a longer service life.

Two hundred grams of allylsilane were polymerized at 70° C. for 3 hours by using a titanium trichloride base catalyst for the polymerization of olefins, thereby obtaining 150 g of powdery polyvinylsilane.

After mixing 6 g of the above polymer with 40 g of SiC powder of the same kind as that employed in Example 23, the resultant mixture was heated and molded into a crucible-like shape in nitrogen. In a vacuum, the crucible-like green body was heated gradually from room temperature to 1,500° C., followed by firing at 1,800° C. for further 4 hours.

The bulk specific gravity of the thus-obtained crucible was 3.09. When the crucible was used for melting polycrystalline silicon, the crucible had a service life improved significantly compared with conventional SiC crucibles. Moreover, single crystals obtained by the pulling method contained extremely little impurities.

EXAMPLE 26

After mixing 10 g of the silicon-containing polymer (c) employed in Example 23 and 40 g of commercial $Si_3N_4$ powder of 400 mesh on average, the resultant mixture was heated and formed into a plate-like shape at 150° C. in nitrogen gas. In a vacuum, the plate-like green body was heated gradually from room temperature to 1,500° C., followed by firing at 1,800° C. for 5 hours.

The bulk specific gravity of the thus-obtained sintered body was 3.02. The impact fracture strength of the sintered body was above 3 times compared with that (bulk specific gravity: 2.94) obtained by using polystyrene in lieu of the silicon-containing polymer (c).

EXAMPLE 27

Polyvinylsilane (e), which had been obtained by polymerizing vinylsilane in the presence of AIBN as a radical polymerization initiator and had an average molecular weight of about 20,000, was spun by the melt-spinning method. The thus-spun fibers were subjected to a infusibilizing treatment at 180° C. in air, whereby fibers having a diameter of 10 μm and made of a high molecular organosilicon compound were obtained. Those fibers were preheated in a vacuum ($1 \times 10^{-3}$ mmHg) by raising its temperature to 1,000° C. over 10 hours. They were then heated in an argon gas atmosphere to 1,200° C., at which they were subjected to high-temperature firing for 2 hours to obtain SiC fibers. The ceramics yield was 48% in the production of the fibers. The tensile strength of the fibers was 750 Kg/mm². The fired product was fired further at 2,000° C. and was then analyzed by X-ray diffractometry. No diffraction peak characteristic of free carbon was observed.

EXAMPLES 28 & 29

Polypropylsilane and polybutenylsilane obtained separately in the same manner as in Examples 20 and 21 were individually dissolved in toluene. They were separately spun by the dry spinning method, so that fibers having a diameter of 10 μm and made of high molecular organosilicon compounds respectively were obtained. Those fibers were treated in the same manner as in Example 27, thereby obtaining silicon carbide fibers.

Evaluation results are summarized in Table 2.

EXAMPLE 30

SiC fibers were obtained in the same manner as in Example 27 except that the polyvinylsilane (e) was spun by the melt spinning method and then caused to pass for their infusibilization through a dioxane solution maintained at 40° C. and containing 40 wt. % of n-propylamine and 5 wt. % of potassium (time of contact: about 10 minutes).

Evaluation results are shown in Table 2.

COMPARATIVE EXAMPLE 3

SiC fibers were obtained in the same manner as in Example 27 except for the use of polycarbosilane of the same kind as that employed in Comparative Example 2.

Evaluation .results are shown in Table 2.

EXAMPLE 13

The crucible obtained in Example 23 was immersed at room temperature for 2 days in a benzene solution which contained the oily polyvinylsilane (c) at a concentration of 50 wt. %. Benzene was then eliminated. The crucible was thereafter heated in a vacuum while gradually raising the temperature from room temperature to 1,500° C., followed by firing at 1,800° C. for 4 days. This operation was repeated three times. The bulk specific density was 3.15. The mechanical strength of the crucible was about twice as strong as the crucible obtained in Example 23 before its treatment, thereby improving the service life considerably.

TABLE 1

| Example | Synthesis of polymer | | | | Silicon carbide ceramics obtained | | |
|---|---|---|---|---|---|---|---|
| | Monomer polymerized | Yield of polymer | Property of polymer and its evaluation | | Average M.W. | Yield of* ceramics | Impurities in fired body |
| | | | Polymer structure | Property of polymer | | | |
| 17 | $CH_2=CH-SiH_3$ | 51 | $+CH_2-CH+$ <br> $\|$ <br> $SiH_3$ | m.p. 170–180° C. | 100,000 | 79% | Free carbon not observed |
| 18 | " | " | " | " | " | 96% | Free carbon not observed |
| 19 | " | 96 | " | Oily | 3,000 | 69% | Free carbon not observed |
| 20 | $CH_2=CH-CH_2-SiH_3$ | 75 | $+CH_2-CH+$ <br> $\|$ <br> $CH$ <br> $\|$ <br> $SiH_3$ | m.p. 150–160° C. Soluble in heptane, hexane and toluene | 50,000 | 64% | Free carbon: about 2 wt. % |
| 21 | $CH_2=CH-CH_2-CH_2-SiH_3$ | 86 | $+CH_2-CH+$ <br> $\|$ <br> $(CH_2)_2$ <br> $\|$ <br> $SiH_3$ | m.p. about 100° C. Soluble in heptane, hexane and toluene | 30,000 | 59% | Free carbon: about 5 wt. % |

TABLE 1-continued

| | Synthesis of polymer | | | Property of polymer and its evaluation | | Silicon carbide ceramics obtained | | |
|---|---|---|---|---|---|---|---|---|
| | Monomer polymerized | | Yield of polymer | Polymer structure | Property of polymer | Average M.W. | Yield of* ceramics | Impurities in fired body |
| 22 | $CH_2=CH-Si_2H_5$ | | 44 | $+CH_2-CH+$ <br> $\|$ <br> $Si_2H_5$ | m.p. 140–150° C. | 70,000 | 72% | Free carbon not observed |
| Comp. Ex. | | | | | | | | |
| 1 | Commercial product | | | $\left(\begin{array}{c}CH_3\\ \|\\ -Si-\\ \|\\ CH_3\end{array}\right)$ | Infusible. Insoluble in solvents. | 2,000–3,000 | 6% | Free carbon not observed |
| 2 | Commercial product used in Comp. Ex. 1 was modified thermally. | | | $\left(\begin{array}{c}CH_3\\ \|\\ -Si-CH_2-\\ \|\\ H\end{array}\right)$ | m.p. 233° C. Soluble in benzene | 2,000 | 53% | Free carbon: about 10 wt. % |

*On Si basis.

TABLE 2

| | Polymer structure | Property of polymer | Average M.W. | Si-basis yield of ceramics upon fiber production | Tensile strength of fibers, Kg/mm² | Impurities in fired body |
|---|---|---|---|---|---|---|
| Example | | | | | | |
| 27 | $+CH_2-CH+$ <br> $\|$ <br> $SiH_3$ | m.p. 170–180° C. | 20,000 | 48 wt. % | 790 | Free carbon not observed. $SiO_2$: 6 wt. % |
| 28 | $+CH_2-CH+$ <br> $\|$ <br> $CH$ <br> $\|$ <br> $SiH_3$ | m.p. 150–160° C. Soluble in heptane, hexane and toluene. | 50,000 | 30 wt. % | 550 | Free carbon: about 2 wt. % $SiO_2$: 5 wt. % |
| 29 | $+CH_2-CH+$ <br> $\|$ <br> $(CH_2)_2$ <br> $\|$ <br> $SiH_3$ | m.p. about 100° C. Soluble in heptane, hexane and toluene. | 30,000 | 21 wt. % | 400 | Free carbon: about 5 wt. % $SiO_2$: 8 wt. % |
| 30 | $+CH_2-CH+$ <br> $\|$ <br> $SiH_3$ | m.p. 170–180° C. | 20,000 | 48 wt. % | 810 | Free carbon not observe. $SiO_2$: 1 wt. % |
| Comp. Ex. 3 | $\left(\begin{array}{c}CH_3\\ \|\\ -Si-CH_2-\\ \|\\ H\end{array}\right)$ | m.p. 233° C. Soluble in benzene. | 1,800 | 39 wt. % | 320 | Free carbon: about 10 wt. % $SiO_2$: 17 wt. % |

This invention provides an economical and novel route for the synthesis of alkylsilanes or alkenylsilanes, whose demand is expected as new raw materials for the organosilicon industry, by using $SiH_4$, $Si_2H_6$ or $Si_3H_8$ whose industrial production has started reflecting the development of the semiconductor industry in recent years and which have hence become available at low prices. The silanes according to the present invention are novel materials. They can of course 10 substitute more suitably for conventional basic raw materials of the alkylchlorosilane type. In addition, owing to the high reactivity of Si—H bonds and the characteristic properties of Si—Si bonds, it is possible to impart still higher functionality. They are non-chlorine silanes. Owing to these advantageous features, the silanes according to this invention materialize the development of more meritorious and new industrial processes for organosilicons.

This invention also provides a process for the production of novel silicon-containing polymers which are useful industrially. Specifically, this invention primarily features inexpensive monomers and their economical polymerization process. In view of the specific physical properties and reactivity of the resulting polymers, especially, silyl groups, various functions (applications) are expected, especially, including prepolymers for ceramics (SIC), modifiers for various polymers, raw materials for IPN, surface treatment agents, etc. by way of example. For example, functions such as crosslinkability, foamability and reactivity with other monomers or polymers may be imparted to conventional polymers such as styrene and polyvinyl chloride, especially, by using the reactivity of silyl groups, thereby making a significant contribution to the creation of new high function materials.

Furthermore, the present invention also provides novel silicon-containing high molecular compounds containing the above-mentioned silyl groups and a process for the production of silicon carbide ceramics by using the high molecular compounds as prepolymers. The prepolymers containing silyl groups, which are useful in the present invention, are excellent in plasticity, solvent solubility and the like and permit easy processing. Moreover, they enjoy higher ceramics yields compared with conventional prepolymers (polysilane, polycarbosilane, etc.). In addition, little free carbon is contained in ceramics to be obtained upon firing. The prepolymers have such excellent characteristic features. Different from the conventional compression-molding method for ceramics powder which requires large equipment, the specific, easily-processable, silicon-containing, high-molecular compounds specified in the present invention are used as prepolymers. It is hence possible to obtain molded ceramics bodies of silicon carbide having a desired shape by molding or otherwise forming the high-molecular compounds either as is or subsequent to their mixing and kneading-with ceramics powder and then firing the thus-molded or formed green bodies.

When SiC fibers or the like are produced in particular, the fibers have smaller silica or carbon content compared with conventional fibers obtained by using polycarbosilane as a prepolymer, thereby exhibiting high-temperature strength far superior to conventional SiC fibers.

We claim:

1. A process for the preparation of a silicon-containing polymer which comprises subjecting, to anionic coordination polymerization, a silicon compound represented by the following formula:

$$CH_2=CR_1$$
$$|$$
$$(R_2)_m Si_n H_{2n+1}$$

wherein m is 0 or a positive integer of 1 to 20, n stands for 2 or 3, $R_1$ means hydrogen, an alkyl group, an aryl group or a halogen, $R_2$ denotes an alkylene or phenylene group, and $R_1$ and $R_2$ may contain one or more functional groups such as COOH, $NH_2$, Cl and OH, the silicon-containing polymer containing recurring structural units represented by the following general formula:

$$+CH_2-CR_1+$$
$$|$$
$$(R_2)_m$$
$$|$$
$$Si_n H_{2n+1}$$

wherein m is 0 or a positive integer of 1 to 20, n stands for 2 or 3, $R_1$ means hydrogen, an alkyl group, an aryl group or a halogen, $R_2$ denotes an alkylene or phenylene group, and $R_1$ and $R_2$ may contain one or more functional groups such as COOH, $NH_2$, Cl and/or OH.

2. A process for the preparation of a silicon-containing polymer containing recurring structural units represented by the following formula:

$$+CH_2-CR_1+$$
$$|$$
$$(R_2)_m$$
$$|$$
$$Si_n H_{2n+1}$$

wherein m is 0 or a positive integer of 1 to 20, n stands for 1, 2, or 3, $R_1$ means hydrogen, an alkyl group, an aryl group or a halogen, $R_2$ denotes an alkylene or phenylene group, and $R_1$ and $R_2$ may contain one or more functional groups such as COOH, $NH_2$, Cl and OH, which comprises subjecting, to either radical polymerization or ionic polymerization, a silicon compound represented by the following formula:

$$CH_2=CR_1$$
$$|$$
$$(R_2)_m Si_n H_{2n+1}$$

wherein m, n, $R_1$ and $R_2$ have the same meaning as defined above.

3. A process for the preparation of a silicon-containing polymer, which comprises subjecting, to radical copolymerization, a silicon compound represented by the following formula:

$$CH_2=CR_1 \qquad (III)$$
$$|$$
$$(R_2)_m Si_n H_{2n+1}$$

wherein m is 0 or a positive integer of 1 to 20, n stands for 1, 2 or 3, $R_1$ means hydrogen, an alkyl group, an aryl group or a halogen, $R_2$ denotes an alkylene or phenylene group, and $R_1$ and $R_2$ may contain one or more functional groups such as COOH, $NH_2$, Cl and OH, and an unsaturated hydrocarbon having at least one carbon-carbon double bond per molecule.

* * * * *

UNITED STATES PATENT AND TRADEMARK OFFICE
CERTIFICATE OF CORRECTION

PATENT NO. : 5,508,363
DATED : Apr. 16, 1996
INVENTOR(S) : Itoh et al.

It is certified that error appears in the above-identified patent and that said Letters Patent is hereby corrected as shown below:

On the title page, under [30] Foreign Application Priority Data, delete all priority applications and insert --Apr. 22, 1987 [JP] Japan ........ 62-097417
          Apr. 23, 1987 [JP] Japan ........ 62-098698
          Jan. 28, 1988 [JP] Japan ........ PCT/JP88/00065--

Signed and Sealed this

Twenty-seventh Day of August, 1996

Attest:

BRUCE LEHMAN

*Attesting Officer*        *Commissioner of Patents and Trademarks*